(12) United States Patent
Stewart et al.

(10) Patent No.: US 7,341,758 B2
(45) Date of Patent: Mar. 11, 2008

(54) METHOD FOR PREPARING AND ULTRASONICALLY TESTING A THERMAL-SPRAY COATED ARTICLE

(75) Inventors: Matthew Stewart, Cincinnati, OH (US); Thomas J. Tomlinson, Cincinnati, OH (US); David J. Dietz, Loveland, OH (US); Patsy Augustine Ruzzo, West Chester, OH (US)

(73) Assignee: General Electric Company, Schenectady, NY (US)

( * ) Notice: Subject to any disclaimer, the term of this patent is extended or adjusted under 35 U.S.C. 154(b) by 679 days.

(21) Appl. No.: 10/422,386

(22) Filed: Apr. 24, 2003

(65) Prior Publication Data

US 2008/0038477 A1    Feb. 14, 2008

(51) Int. Cl.
*C23C 4/18* (2006.01)
*G01N 29/04* (2006.01)
*G01N 29/44* (2006.01)

(52) U.S. Cl. .................... 427/8; 427/446; 427/455; 427/456; 73/588; 73/627

(58) Field of Classification Search ............ 427/8, 427/446, 455, 456; 73/588, 582, 627, 632
See application file for complete search history.

(56) References Cited

U.S. PATENT DOCUMENTS

| | | | | |
|---|---|---|---|---|
| 4,275,124 A | * | 6/1981 | McComas et al. .......... 428/564 |
| 4,292,848 A | * | 10/1981 | Rainey et al. ................ 73/602 |
| 4,655,084 A | * | 4/1987 | Renzel ......................... 73/611 |
| 5,268,045 A | * | 12/1993 | Clare .......................... 148/518 |
| 6,314,819 B1 | | 11/2001 | Nishimura et al. |
| 6,443,012 B2 | | 9/2002 | Beardmore |
| 6,484,583 B1 | | 11/2002 | Chennell et al. |
| 6,534,975 B2 | | 3/2003 | Beeck et al. |

FOREIGN PATENT DOCUMENTS

| | | | |
|---|---|---|---|
| DE | 246 832 A | | 6/1987 |
| DE | 197 52 574 A | | 6/1999 |
| JP | 4-238265 | * | 8/1992 |
| JP | 04-238265 | * | 8/1992 |
| JP | 4238265 A | | 8/1992 |
| JP | 2000-002691 | * | 1/2000 |

OTHER PUBLICATIONS

Abstract of Japan 04-238265, labeled "PAT-No: JP404238265A", copyright 1992.*

* cited by examiner

*Primary Examiner*—Katherine Bareford
(74) *Attorney, Agent, or Firm*—McNees Wallace & Nurick LLC

(57) ABSTRACT

An article having a thermal-spray coating thereon is prepared by thermally spraying a coating material onto a surface of a substrate article. The coated article is nondestructively tested by directing a transmitted ultrasonic signal into the coated article, receiving a received ultrasonic signal from the coated article, and evaluating a near-bondline region of the coated article located adjacent to the surface of the article using the received ultrasonic signal.

12 Claims, 4 Drawing Sheets

RECEIVED ULTRASONIC SIGNAL

RECEIVED ULTRASONIC SIGNAL

RECEIVED ULTRASONIC SIGNAL

METHOD FOR PREPARING AND ULTRASONICALLY TESTING A THERMAL-SPRAY COATED ARTICLE

This invention relates to the preparation of articles having a thermal-spray coating thereon, and more particularly to the testing of such articles to ensure the integrity of the bond between the coating and the article substrate.

BACKGROUND OF THE INVENTION

Metallic coatings may be applied to substrates using a thermal-spray process. In this process, a coating material, usually provided in a power or wire form, is heated to an elevated temperature in a spray device. The coating material may be entirely melted to form liquid droplets, may be partially melted to form semiplastic particles, or may be unmelted solid powder particles. The heated coating material is ejected from the spray device at a high velocity and thence sprayed against a substrate article surface. The sprayed material deposits upon the surface and, to the extent that it is liquid, solidifies. The droplets and particles impact the surface at a high velocity, and are flattened against the surface. The deposition continues until the solidified coating has reached a desired thickness, often as great as about 0.150 inches.

The thermal-spray process is highly versatile. It may be used with a wide variety of compositions and substrate articles, yielding a variety of different types of properties. In one example, to build up an article that has been partially worn away during prior service, the coating material may have the same compositions as the substrate article. In another example, to provide a wear-resistant coating at the surface, the coating has a different composition than the substrate article and is more wear resistant than the substrate article. In yet another example, to provide a wearing or abradable coating at the surface, the coating has a different composition than the substrate article and is less wear resistant than the substrate article. The thermal-spray process may be used to coat irregular and complexly shaped article substrates.

For most of its applications, the thermally sprayed coating must adhere very well at a bondline to the entire surface to which it is applied, with a good mechanical bond. There may not be delaminations of the coating from the substrate, where a region of the coating is completely separated from the substrate. In some more-demanding applications, the coating must further be metallurgically bonded to the substrate.

The usual approach to determining the nature of the bonding of the sprayed coating to the substrate is destructive sectioning of the coated article and metallurgical inspection of the bondline region. This approach is normally applied to establish process parameters that achieve a good bonded coating, and then the same process parameters are used in the production coating operations. This approach has the drawback that, because the thermal-spray process is so versatile, it is difficult to perform the destructive testing over the entire range of possible types of coatings and configurations of substrate articles. Even if a process is established as acceptable with the destructive testing of test coupons, relatively minor variations in production parameters may lead to unacceptable bondline structures in the production articles. Another problem with the use of test coupons in this circumstance is that the test coupons may behave differently than the production parts. Post-coating operations such as heat treating and machining may introduce bondline defects to initially defect-free bondlines.

There is a need for an improved approach to the thermal-spray coating process and the evaluation of the bondline region of the coated article. The present invention fulfills this need, and further provides related advantages.

SUMMARY OF THE INVENTION

The present invention provides a coated article having a thermal-spray coating thereon. The nature of the near-bondline region between the coating and the substrate article is evaluated nondestructively, precisely, and rapidly. Actual production hardware of simple or complex shapes, and with a wide variety of coating/substrate article combinations, may be readily evaluated to be certain that the coating is well bonded to the article substrate.

A method for preparing an article having a thermal-spray coating thereon comprises the steps of providing a substrate article having a surface, and forming a coated article. The step of forming includes the step of thermally spraying a coating material onto the surface of the substrate article, with the surface of contact between the coating material and the substrate article being a bondline. Examples of thermal-spray processes include high velocity oxyfuel spray, air plasma spray, low-pressure-plasma spray, electric wire arc spray, and combustion wire or powder spray. Optionally, the article with the thermally sprayed coating thereon is heat treated after the step of thermally spraying. The method further includes nondestructively testing the coated article by directing a transmitted ultrasonic signal into the coated article, receiving a received ultrasonic signal from the coated article, and evaluating a near-bondline region of the coated article located adjacent to the bondline using the received ultrasonic signal.

In an application of interest, the substrate article is a component of a gas turbine engine. The substrate article may be of any operable type, but metallic alloys such as nickel-base alloys, iron-base alloys, titanium-base alloys, and cobalt-base alloys are of particular interest. The thermally sprayed coating material is of any operable type, but is preferably a material such as NiCrAl. The thickness of the thermal-spray coating may be any operable value, but is typically from about 0.002 inch to about 0.150 inch.

The transmitted ultrasonic signal may be of any operable frequency, but is preferably of a frequency of from about 5 MHZ (megahertz) to about 20 MHZ. The received ultrasonic signal may be either reflected or transmitted, but is preferably reflected. The spatial region of interest in the received ultrasonic signal may be isolated by establishing a spatial (time) gate in the received ultrasonic signal to define the near-bondline region.

In the most basic approach, the evaluation of the near-bondline region from the received ultrasonic signal generally falls into three main categories. If there is no return in the received ultrasonic signal received from the bondline region, it may be concluded that there is no delamination (i.e., no complete separation) of the coating from the substrate article, and there is a metallurgical bond between the coating and the substrate. If there is a strong ultrasonic return in the received ultrasonic signal at the bondline, it may be concluded that there is a delamination at the bondline where the coating and the substrate are no longer in intimate contact. If there is a weak ultrasonic return received from the bondline, it may be concluded that there is no delamination, the coating is in intimate contact with the substrate but there is no metallurgical bond, and instead a mechanical bond. In all cases, there is an ultrasonic return from the front surface. A "return" is a peak in the received ultrasonic signal, and is distinct from the background of the received ultrasonic signal. As used herein for a preferred acceptability criterion, a "strong" return from the near-bondline region has a amplitude of more than about 25 percent of the amplitude of a return from a back surface of a calibration specimen of the substrate material about 0.250 inch thick, and a "weak" return has a substantially nonzero amplitude of not more than about 25 percent of the amplitude of a return from the back surface of the calibration specimen of the substrate material about 0.250 inch thick. In some cases, a mechanical bond is made into a metallurgical bond by increased interdiffusion of the coating material and the substrate article during heat treatment.

The present approach provides a reliable, highly reproducible approach for preparing high-quality articles with thermally sprayed coatings thereon. The technique may be used in conjunction with a wide variety of shapes and sizes of substrate articles, for a wide variety of compositions of substrate articles and coatings, particularly for coating thicknesses greater than about 0.020 inch, for all known types of thermal-spray processes, and for both heat-treated and non-heat-treated substrate-and-coating combinations. The testing and evaluation associated with the process are completely nondestructive, so the approach may be used with each piece of production hardware and not just with test specimens.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
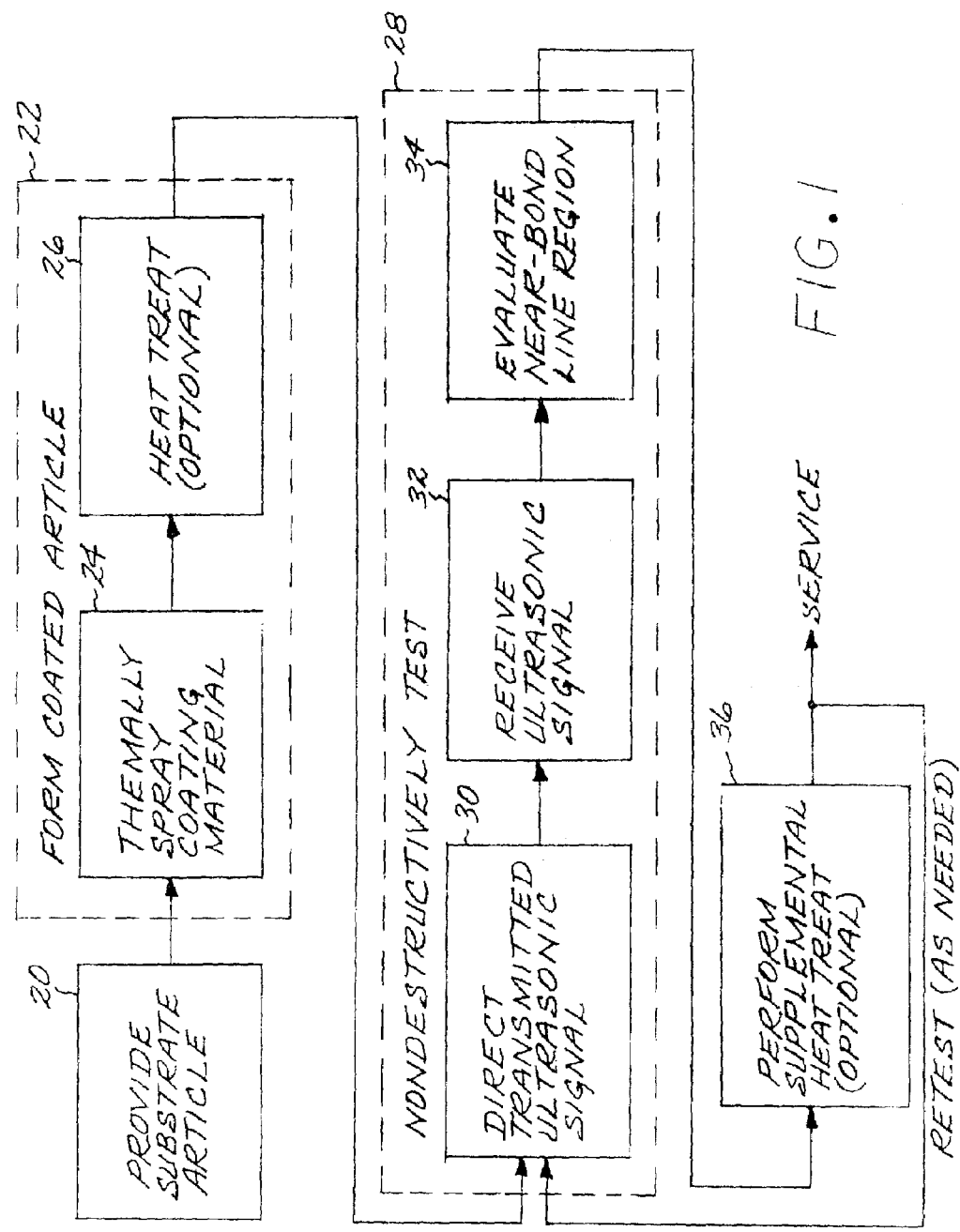
FIG. 1 is a block flow diagram of a method for preparing an article having a thermal-spray coating thereon.

FIG. 1 depicts a preferred approach for practicing the present method. A substrate article is furnished, step 20. The substrate article may be of any operable shape, size, and configuration. Examples of substrate articles of interest include areas of components of gas turbine engines such as seals and flanges, as well other types of articles. The substrate article may be made of any operable base material. Examples of operable base materials include nickel-base alloys, which have more nickel by weight than any other element; cobalt-base alloys, which have more cobalt by weight than any other element; titanium-base alloys, which have more titanium by weight than any other element; iron-base alloys, which have more iron by weight than any other element; and aluminum-base alloys, which have more aluminum by weight than any other element. An example of a nickel-base alloy of particular interest is Alloy 718, having a specification composition, in weight percent, of from about 50 to about 55 percent nickel, from about 17 to about 21 percent chromium, from about 4.75 to about 5.50 percent columbium plus tantalum, from about 2.8 to about 3.3 percent molybdenum, from about 0.65 to about 1.15 percent titanium, from about 0.20 to about 0.80 percent aluminum, 1.0 percent maximum cobalt, and balance iron totaling 100 percent by weight. Small amounts of other elements such as carbon, manganese, silicon, phosphorus, sulfur, boron, copper, lead, bismuth, and selenium may also be present. These substrate articles and compositions are presented by way of examples of preferred embodiments, and not by way of limitation.

Figure 2:
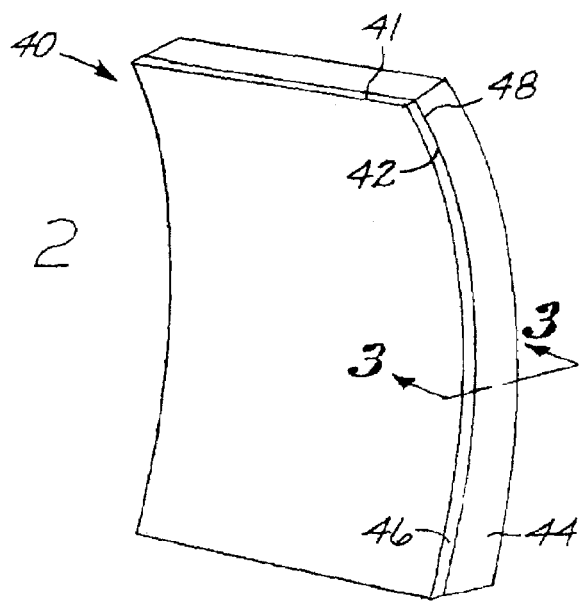
FIG. 2 is a perspective view of a coated article.
Figure 3:
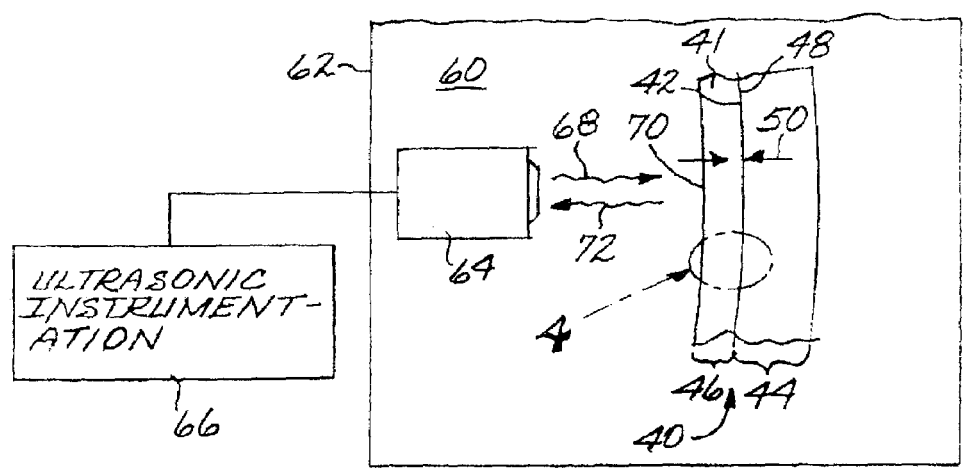
FIG. 3 is a schematic sectional view of the coated article of FIG. 2, taken on line 3-3, during ultrasonic testing.

A coated article 40, as shown in FIGS. 2-3, is formed, step 22. In the illustration, the coated article 40 is an idealized view of a segment of a circumferential gas-path seal of a gas turbine engine. The forming step 22 includes the step 24 of thermally spraying a coating material 41 onto a surface 42, in this case the inwardly facing surface that faces the gas path, of the substrate article 44 to form a thermal-spray coating 46. A surface of contact between the coating material 41 and the coating 46, on the one hand, and the substrate article 44, on the other, is a bondline 48. The coating material 41 may be any operable material. An example of a preferred coating material 41 for use in a seal application on an Alloy 718 substrate is NiCrAl, having a nominal composition range, in weight percent, of from about 4.5 to about 7.5 percent aluminum, from about 15.5 to about 20.5 percent chromium, 3 percent maximum manganese, 1 percent maximum iron, 0.3 percent maximum carbon, 2 percent maximum silicon, 3.5 percent maximum of other elements, balance nickel but preferably 70 percent minimum nickel. The coating 46 may be any operable thickness, and a typical thickness range is from about 0.002 inch to about 0.150 inch. The present approach is preferably used with coating thicknesses of from about 0.020 inch to about 0.150 inch.

The thermal-spraying step 24 may be performed by any operable approach, and a number of thermal-spray techniques are known in the art. Examples include high velocity oxyfuel spray (HVOF), air plasma spray (APS), low-pressure-plasma spray (LPPS), electric wire arc spray, and combustion wire or powder spray. Briefly, in HVOF, high-velocity flows of fuel gas and an oxidizer are combusted to produce a high temperature in an HVOF deposition gun, and a flow of the coating material in powdered form is fed into the combustion-gas stream. In APS and LPPS, a plasma is created, as by an electric arc or a high-intensity laser beam, and the coating material in powdered form is fed into the plasma and thence sprayed against the substrate article. APS is performed at essentially atmospheric pressure with an inert shield gas to prevent oxidation of the coating material, and LPPS is performed at reduced pressure to minimize the oxidation. The thermal-spray step 24 is continued until the desired thickness of the thermal-spray coating 46 is reached.

Optionally, the coated article 40, including the substrate article 44 with the thermal-spray coating 46 thereon, may be heat treated, step 26, after the thermal-spray step 24 is complete. Any operable heat treatment may be used. In the case of the example discussed above, the deposition of NiCrAl onto Alloy 718, the heat treatment is preferably at a temperature of about 1700-1925° F. and for a time of about 1-48 hours. The heat treatment causes the coating material 41 to interdiffuse to some degree with the base material of the substrate article 44. The coated article 40 may be machined as necessary either before or after heat treating.

Ideally, these steps 20-26 would produce an acceptable coated article 40 every time. However, in practice, a wide variety of factors, such as the shape of the substrate article 44, the base material of the substrate article 44 and the coating material 41, and variations in operating parameters may cause the coated article 40 to have flaws in a near-bondline region 50 thereof, adjacent to and encompassing the bondline 48. Such flaws may cause the thermal-spray coating 46 to perform in an unsatisfactory manner. It is therefore important to determine when such flaws are present, and when the coated article 40 is free of such flaws.

To make that determination, the coated article 40 is nondestructively tested, step 28, by an ultrasonic technique. A transmitted ultrasonic signal is directed into the coated article, step 30, and a received ultrasonic signal is received from the coated article, step 32. FIG. 3 depicts one form of an ultrasonic apparatus for performing this inspection. In this apparatus, the coated article 40 is immersed in an ultrasonic-transmitting fluid 60, in this case water, in a tank 62. An ultrasonic transducer 64 having ultrasonic instrumentation 66 generates the transmitted ultrasonic signal 68 directed through the fluid 60 toward the coated article 40. The transmitted ultrasonic signal 68 is focused at a front surface 70 of the coated article 40 facing the ultrasonic transducer 64. The transmitted ultrasonic signal 68 is propagated into the coated article 40, and reflects from features therein. The reflected ultrasonic signal propagates back out of the coated article 40 through the front surface 70, through the fluid 60, and to the ultrasonic transducer 64 as a received ultrasonic signal 72. (Any ultrasonic signal from the backwall of the article is not seen, because a spatial gate, which is also a time gate, in the ultrasonic instrumentation 66 is used to eliminate signals that are far outside the time and position ranges of interest. The spatial gate usually corresponds to the near-bondline region 50.) The received ultrasonic signal 72 is processed by the ultrasonic instrumentation 66. The presently preferred approach as illustrated in FIG. 3 is a reflective ultrasonic technique, selected for convenience and because the near-bondline region 50 of interest is relatively near to the front surface 70. However, a transmission technique, where the received ultrasonic signal 72 is propagated through the substrate article 44 to an ultrasonic receiver located on the apposite side of the coated article 40 from an ultrasonic transmitter may be used. Other operable techniques such as a reflection or transmission contact probe apparatus may also be used.

Figure 4:
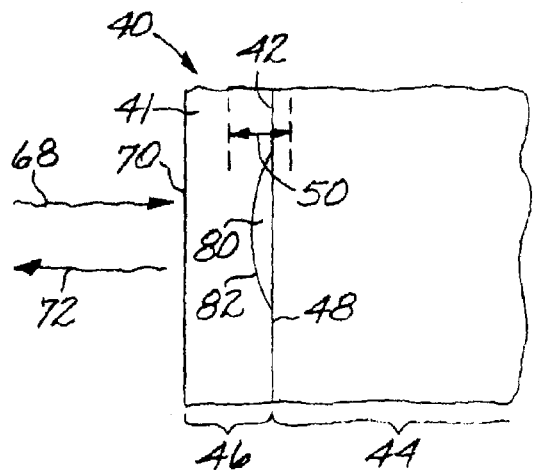
FIG. 4 is a schematic enlargement of the region 4 of FIG. 3, with a bondline delamination present.
Figure 5:
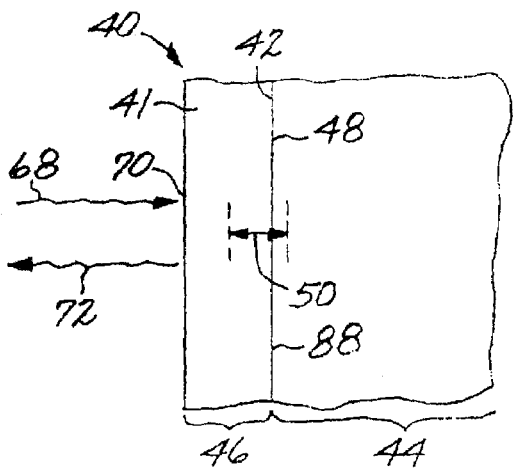
FIG. 5 is a schematic enlargement of the region 4 of FIG. 3, with an intimate coating-substrate contact in a mechanical, but not metallurgical, bond present.
Figure 6:
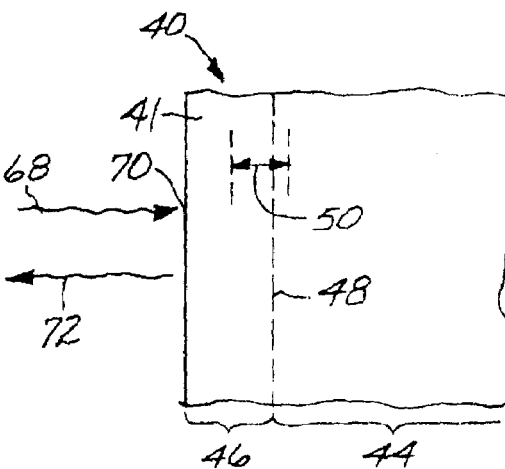
FIG. 6 is a schematic enlargement of the region 4 of FIG. 3, with no bondline delamination present and a metallurgical bond at the bondline.
Figure 7:
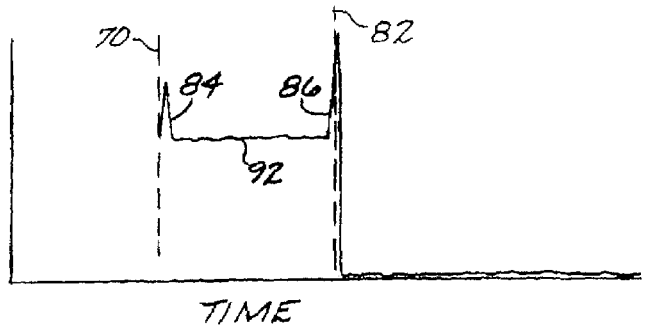
FIG. 7 is a schematic graph of received ultrasonic signal as a function of time for the structure of FIG. 4.
Figure 8:
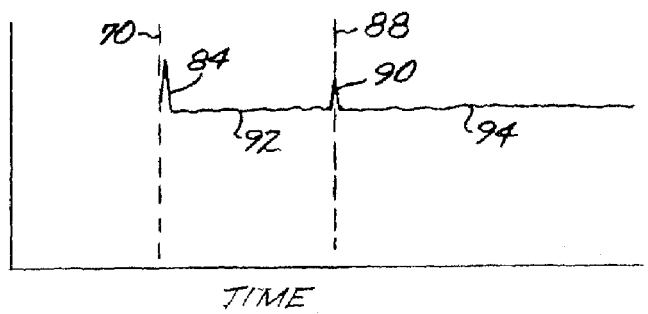
FIG. 8 is a schematic graph of received ultrasonic signal as a function of time for the structure of FIG. 5.
Figure 9:
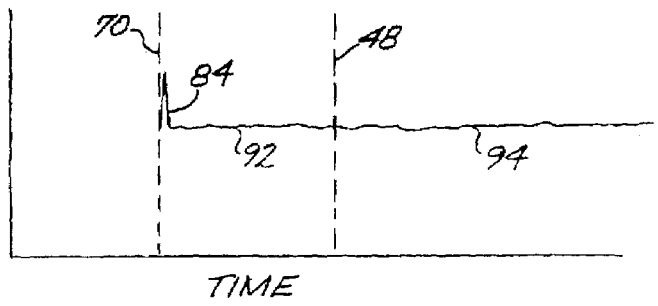
FIG. 9 is a schematic graph of received ultrasonic signal as a function of time for the structure of FIG. 6.

The received ultrasonic signal 72 is evaluated, step 34. The purpose of the ultrasonic evaluation 34 is to determine whether the near-bondline region 50 is delaminated, exhibits a mechanical bond (with no delamination), or exhibits a metallurgical bond (with no delamination). FIGS. 4-6 illustrate the three primary types of structures that are observed, and FIGS. 7-9 respectively illustrate the associated general forms of the received ultrasonic signal. FIGS. 7-9 are idealized ultrasonic forms to show the nature of the received ultrasonic signal and returns therein. A "return" is a peak in the background signal that is discernibly different from the background signal. As used herein for a preferred acceptability criterion, a "strong" return from the near-bondline region has a amplitude of more than about 25 percent of the amplitude of a return from a back surface of a calibration specimen of the substrate material about 0.250 inch thick, and a "weak" return has a substantially nonzero amplitude of not more than about 25 percent of the amplitude of a return from the back surface of the calibration specimen of the substrate material about 0.250 inch thick. In some cases, a mechanical bond is transformed into a metallurgical bond by increased interdiffusion of the coating material and the substrate article during heat treatment. In normal practice, a spatial (or, equivalently, a time) gate is applied to the received ultrasonic signal 72 so as to view only the portion that corresponds to the near-bondline region 50. The following discussion applies to the received ultrasonic signal in the lateral region where the type of structure under discussion is present, here the near-bondline region 50 in a specific lateral area. For example, a delamination may extend laterally over a relatively small area, so that there is a strong return ultrasonic signal from the near bondline in that area, but there is no return in the ultrasonic signal from the near bondline in neighboring areas that have no delamination.

FIG. 4 illustrates a structure having a bondline delamination 80 wherein the thermal-spray coating 46 is physically separated from the surface 42, leaving a gap therebetween. The corresponding received ultrasonic signal 72 illustrated in FIG. 7 shows a return 84 from the front surface 70, a background signal 92 from the coating material 41, and a strong return 86 from a near surface 82 of the bondline-delamination 80. There is no background signal from the substrate article 44, because the ultrasonic signals 68 and 72 do not propagate across the bondline delamination 80 to any substantial degree. The strong return 86 for a delamination is usually very much greater than the background signals 92 and 94.

FIG. 5 illustrates a structure with a coating-substrate contact (i.e., no delamination) and mechanical bond 88, but no metallurgical bond. The thermal-spray coating 46 is not physically separated from the surface 42, as in FIG. 4, but instead there is a metallurgical discontinuity associated with the presence of an interface that is mechanically but not fully metallurgically bonded between the thermal-spray coating 46 and the substrate article 44, at the bondline 48. The corresponding received ultrasonic signal 72 illustrated in FIG. 8 shows the front-surface return 84, and additionally a weak return 90 from the mechanical bond 88. There is a background signal 92 from the coating material 41 and a background signal 94 from the substrate article 46, because the mechanical bond 88 does pass the ultrasonic signals 68 and 72.

FIG. 6 illustrates a structure wherein there is no bondline delamination and a metallurgical bond between the coating material 41 and the substrate article 44. When a metallurgical bond is present, generally there is interdiffusion and/or grain growth across the bondline 48 between the coating and the substrate, while these do not occur or occur only incidentally in a mechanical bond. The corresponding received ultrasonic signal 72 illustrated in FIG. 9 shows the front-surface return 84, the background signal 92 from the coating material 41, and the background signal 94 from the substrate article 44, and no return from the area of the bondline 48. The location of the original bondline 48 is indicated in FIG. 9 for reference by a dashed line, but in fact its presence and location cannot be discerned from the received ultrasonic signal 72 in FIG. 9.

The structures of FIGS. 4-6 illustrate a progression from a highly imperfect, delaminated near-bondline region 50 in FIG. 4, which is usually considered to be unacceptable for all applications; to a mechanically bonded near-bondline region 50 in FIG. 5, which is considered to be acceptable for many thermal spray applications; to a high-quality metallurgical bond in the near-bondline region 50 in FIG. 6, which is required for the most-demanding applications. If a structure like that of FIG. 4 is prepared, the coated article 40 must be discarded or, if possible, the bondline delamination 80 may be repaired as by hot isostatic pressing of the coated article 40 to close the bondline delamination 80, or other suitable technique such as shoot-peen densification and re-heattreat or localized weld repair, or the like. The structure of FIG. 5 is acceptable for most applications. Alternatively, it may in some cases be modified to be like that of FIG. 6 by instituting the optional heat treatment 26, or if it is already in use, lengthening the time of or increasing the temperature of the heat treatment 26 (as long as those changes are compatible with other heating treating requirements and/or limitations of the substrate article 44 and the coating material 41). A supplemental heat treatment 36 may also be used following the nondestructive testing 28, particularly if some articles are tested and others are not. The unacceptable articles may be provided the supplemental heat treatment 36, while the acceptable articles are not further heat treated, and the previously unacceptable articles may be retested in the nondestructive test 28. The additional heat treatment 26 and/or 36 causes the thermal-spray coating 46 and the substrate article 44 to interdiffuse, thereby gradually eliminating the magnitude of the weak ultrasonic return 90.

The technique just described for the evaluation of the bonding between the coating material 41 and the substrate article 44 uses only the relative height, if present, or the absence, of an ultrasonic return (i.e., peak) from the near-bondline region 50. This technique provides a straightforward, readily applied non-destructive evaluation procedure and acceptance criterion for the acceptability of bonds. For some cases, a more-complex analysis involving other portions of the received ultrasonic signal, return peak-height ratios, and the like may be used. The actual nature of the near-bondline region 50 varies over a continuum from delamination to mechanical bonds of various strengths, to a metallurgical bond, and the present approach may be used to evaluate the entire continuum. For industrial practice, in most cases it is sufficient to use the three categories, with a strong return from the near-bondline region indicating a delamination, a weak return indicating a mechanical bond, and substantially no return indicating a metallurgical bond.

For the presently preferred practice of the invention, an acceptance criterion was established defining the "strong" return from the near-bondline region as having a amplitude of more than about 25 percent of the amplitude of the return from the back surface of the calibration specimen of the substrate material about 0.250 inch thick, and the "weak" return as having a substantially nonzero amplitude of not more than about 25 percent of the amplitude of the return from the back surface of the calibration specimen of the substrate material about 0.250 inch thick. Other acceptance criteria may be defined as desired. In some processing, any ultrasonic return from the near-bondline region of greater than some selectable amount is unacceptable. In other cases, the distinction between a strong return, a weak return, and substantially no return may be defined in any acceptable manner.

The nondestructive testing 28 may be used both as a process-development tool to determine the required processing of the thermally sprayed article, and as an acceptance test on production hardware to determine its acceptability.

The present approach has been reduced to practice and the operability of the ultrasonic technique verified in comparisons with destructive testing. For example, to detect delaminations, standard holes used for ultrasonic calibration have been installed at the interfaces of samples and reliably detected by their strong returns. Also, delaminations have been detected by ultrasonic testing and then verified by preparing a section through the region that indicated a delamination. Microscopic inspection verified the presence of the delaminations. The ultrasonic inspection technique has also been applied to mechanically bonded coatings that produced a weak return from the near-bondline region 50, with the interface reliably found. The specimen was thereafter heat treated to create a metallurgical bond, with the result that there was no return ultrasonic signal. A sound metallurgical bond was verified by destructive analysis in this testing.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for preparing an article having a thermal-spray coating thereon, comprising the steps of
   providing a substrate article having a surface;
   forming a coated article, the step of forming including the step of
      thermally spraying a coating material onto the surface of the substrate article, wherein a surface of contact between the coating material and the substrate article is a bondline; and
   nondestructively testing the coated article, wherein the step of nondestructively testing includes the steps of
      directing a transmitted ultrasonic signal into the coated article,
      receiving a received ultrasonic signal from the coated article, and
      evaluating a near-bondline region of the coated article located adjacent to the bondline using the received ultrasonic signal, wherein the step of evaluating includes the steps of
         establishing a spatial gate in the received ultrasonic signal to define the near-bondline region,
         concluding the presence of a delamination if there is a strong return in the received ultrasonic signal from the near-bondline region, and
         concluding the presence of a mechanical bond if there is a weak return in the received ultrasonic signal from the near-bondline region.

2. The method of claim 1, wherein the step of providing includes the step of
   providing the substrate article that is a component of a gas turbine engine.

3. The method of claim 1, wherein the step of providing includes the step of
   providing the substrate article that is made of a nickel-base alloy or a cobalt-base alloy.

4. The method of claim 1, wherein the step of forming includes the step of
   heat treating the substrate article with the coating material thereon, after the step of thermally spraying.

5. The method of claim 1, wherein the step of thermally spraying includes the step of
   thermally spraying the coating material by high velocity oxyfuel spray, air plasma spray, low-pressure-plasma spray, electric wire arc, combustion wire spray, or combustion powder spray.

6. The method of claim 1, wherein the step of thermally spraying includes the step of
thermally spraying the coating material as a metal.

7. The method of claim 1, wherein the step of thermally spraying includes the step of
thermally spraying the coating material to a thickness of from about 0.002 to about 0.150 inch.

8. The method of claim 1, wherein the step of nondestructively testing includes the step of
directing the transmitted ultrasonic signal at a frequency of from about 5 MHZ to about 20 MHZ.

9. The method of claim 1, wherein the step of nondestructively testing includes the step of
receiving the received ultrasonic signal as a reflected ultrasonic signal.

10. The method of claim 1, wherein the step of evaluating includes the step of
concluding the presence of a metallurgical bond if there is substantially no return in the received ultrasonic signal from the near-bondline region.

11. A method for preparing an article having a thermal-spray coating thereon, comprising the steps of
providing a metallic substrate article having a surface;
forming a coated article, wherein the step of forming includes the steps of
thermally spraying a metallic coating material onto the surface of the substrate article to a thickness of from about 0.002 to about 0.150 inch, wherein a surface of contact between the coating material and the substrate article is a bondline, thereafter
heat treating the substrate article with the coating material thereon; and
nondestructively testing the coated-and-heat-treated article, the step of nondestructively testing including the steps of
directing a transmitted ultrasonic signal into the coated article at a frequency of from about 5 MHZ to about 20 MHZ,
receiving a reflected received ultrasonic signal from the coated article, and
evaluating a near-bondline region of the coated article located adjacent to the bondline using the received ultrasonic signal, wherein the step of evaluating includes the steps of
establishing a spatial gate in the received ultrasonic signal to define the near-bondline region,
concluding the presence of a delamination if there is a strong return in the received ultrasonic signal from the near-bondline region,
concluding the presence of a mechanical bond if there is a weak return in the received ultrasonic signal from the near-bondline region, and
concluding the presence of a metallurgical bond if there is substantially no return in the received ultrasonic signal from the near-bondline region.

12. The method of claim 11, wherein the step of providing includes the step of
providing the substrate article that is a component of a gas turbine engine made of a nickel-base alloy or a cobalt-base alloy.

\* \* \* \* \*